(12) United States Patent
Stuke et al.

(10) Patent No.: US 8,390,804 B2
(45) Date of Patent: Mar. 5, 2013

(54) SURFACE ENHANCED RAMAN SPECTROSCOPY EMPLOYING VIBRATING NANORODS

(75) Inventors: Michael J. Stuke, Palo Alto, CA (US); Alexandre M. Bratkovski, Mountain View, CA (US); Min Hu, Sunnyvale, CA (US); Huei Pei Kuo, Cupertino, CA (US); Jingjing Li, Palo Alto, CA (US); Zhiyong Li, Redwood City, CA (US); Fung Suong Ou, Palo Alto, CA (US); Shih-Yuan (Sy) Wang, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 437 days.

(21) Appl. No.: 12/697,136

(22) Filed: Jan. 29, 2010

(65) Prior Publication Data

US 2011/0188034 A1     Aug. 4, 2011

(51) Int. Cl.
    *G01J 3/44* (2006.01)
(52) U.S. Cl. ...................................................... 356/301
(58) Field of Classification Search ................... 356/301
    See application file for complete search history.

(56) References Cited

U.S. PATENT DOCUMENTS

| | | | |
|---|---|---|---|
| 7,609,377 B2 | 10/2009 | Wu et al. | |
| 2002/0142480 A1* | 10/2002 | Natan | 356/301 |
| 2005/0158870 A1* | 7/2005 | Natan | 436/166 |
| 2006/0192115 A1* | 8/2006 | Thomas et al. | 250/306 |
| 2006/0252065 A1 | 11/2006 | Zhao et al. | |
| 2007/0086001 A1* | 4/2007 | Islam et al. | 356/301 |
| 2007/0166539 A1 | 7/2007 | Zhao et al. | |
| 2008/0024776 A1* | 1/2008 | Bratkovski et al. | 356/301 |
| 2008/0144026 A1* | 6/2008 | Zhao et al. | 356/301 |
| 2009/0098344 A1* | 4/2009 | Tomaru | 428/172 |

OTHER PUBLICATIONS

Clement Yuen et al., "Surface-Enhanced Raman Scattering: Principles, Nanostructures, Fabrications, and Biomedical Applications," Journal of Innovative Optical Health Sciences, vol. 1, No. 2, 2008, pp. 267-284.
J. L. Yao et al., "A complementary study of surface-enhanced Raman scattering and metal nanorod arrays," Pure Appl. Chem., vol. 72, No. 1, 2000, pp. 221-228.
Ralph A. Tripp et al., "Novel nanostructures for SERS biosensing," Nanotoday, vol. 3, No. 3-4, Jun.-Aug. 2008, pp. 31-37.
Motofumi Suzuki et al., "In-line aligned and bottom-up Ag nanorods for surface-enhanced Raman spectroscopy," Applied Physics Letters, vol. 88, 2006, pp. 203121-1 to 203121-3.

* cited by examiner

*Primary Examiner* — Kara E Geisel

(57) ABSTRACT

A surface enhanced Raman spectroscopy (SERS) apparatus, system and method employ a plurality of nanorods configured to vibrate. The apparatus includes the nanorods having tips at free ends opposite an end attached to a substrate. The tips are configured to adsorb an analyte and to vibrate at a vibration frequency. The apparatus further includes a vibration source configured to vibrate the free ends of the nanorods at the vibration frequency in a back-and-forth motion. Vibration of the nanorods is configured to facilitate detection of a Raman scattering signal emitted by the analyte adsorbed on the nanorod tips. The system further includes a synchronous detector configured to receive the Raman signal and to be gated cooperatively with the vibration of the nanorods. The method includes inducing a vibration of the nanorods, illuminating the vibrating tips to produce a Raman signal, and detecting the Raman signal using the detector.

11 Claims, 3 Drawing Sheets

SURFACE ENHANCED RAMAN SPECTROSCOPY EMPLOYING VIBRATING NANORODS

CROSS-REFERENCE TO RELATED APPLICATIONS

N/A

STATEMENT REGARDING FEDERALLY SPONSORED RESEARCH OR DEVELOPMENT

N/A

BACKGROUND

Detection and identification or at least classification of unknown substances has long been of great interest and has taken on even greater significance in recent years. Among advanced methodologies that hold a promise for precision detection and identification are various forms of spectroscopy, especially those that employ Raman scattering. Spectroscopy may be used to analyze, characterize and even identify a substance or material using one or both of an absorption spectrum and an emission spectrum that results when the material is illuminated by a form of electromagnetic radiation (e.g., visible light). The absorption and emission spectra produced by illuminating the material determine a spectral 'fingerprint' of the material. In general, the spectral fingerprint is characteristic of the particular material or its constituent elements facilitating identification of the material. Among the most powerful of optical emission spectroscopy techniques are those based on Raman-scattering.

Raman-scattering optical spectroscopy employs an emission spectrum or spectral components thereof produced by inelastic scattering of photons by an internal structure of the material being illuminated. These spectral components contained in a response signal (e.g., a Raman signal) may facilitate determination of the material characteristics of an analyte species including identification of the analyte.

Unfortunately, the Raman signal produced by Raman-scattering is extremely weak in many instances compared to elastic or Rayleigh scattering from an analyte species. The Raman signal level or strength may be significantly enhanced by using a Raman-active material (e.g., Raman-active surface), however. For example, a surface that includes a Raman-active material may be employed in surface enhanced Raman-scattering (SERS) optical spectroscopy to significantly enhance a signal level or intensity of the Raman signal produced by a particular analyte species. While SERS has proven to yield good results in many applications, further improvements are still being sought.

For example, SERS often suffers from or exhibits unpredictable hot spots across the surface. The hot spots produce much higher-level Raman signals than surrounding areas but the location and quantity of these hot spots can be difficult to control. As such, it is often necessary to flood the entire surface with analyte to insure that sufficient analyte reaches the hot spots and produces a detectable Raman signal. Requiring the surface to be flooded precludes detection of very small amounts of analyte (e.g., single molecules) and also hinders identifying other analyte characteristics such as species distribution within a sample.

Attempts to localize or control the production of hot spots have included the use of sharp tips in conjunction with a SERS surface in what is known as tip enhanced Raman spectroscopy (TERS). In TERS, a sharp, conductive tip is placed very close to but spaced apart from the SERS surface. The tip acts as an antenna concentrating and locally enhancing the electromagnetic field in a region between the tip and the surface. While producing results including detection of extremely small quantities of analyte, TERS presents many practical challenges to implementation and use.

BRIEF DESCRIPTION OF THE DRAWINGS

The various features of embodiments of the present invention may be more readily understood with reference to the following detailed description taken in conjunction with the accompanying drawings, where like reference numerals designate like structural elements, and in which.

Figure 1A:
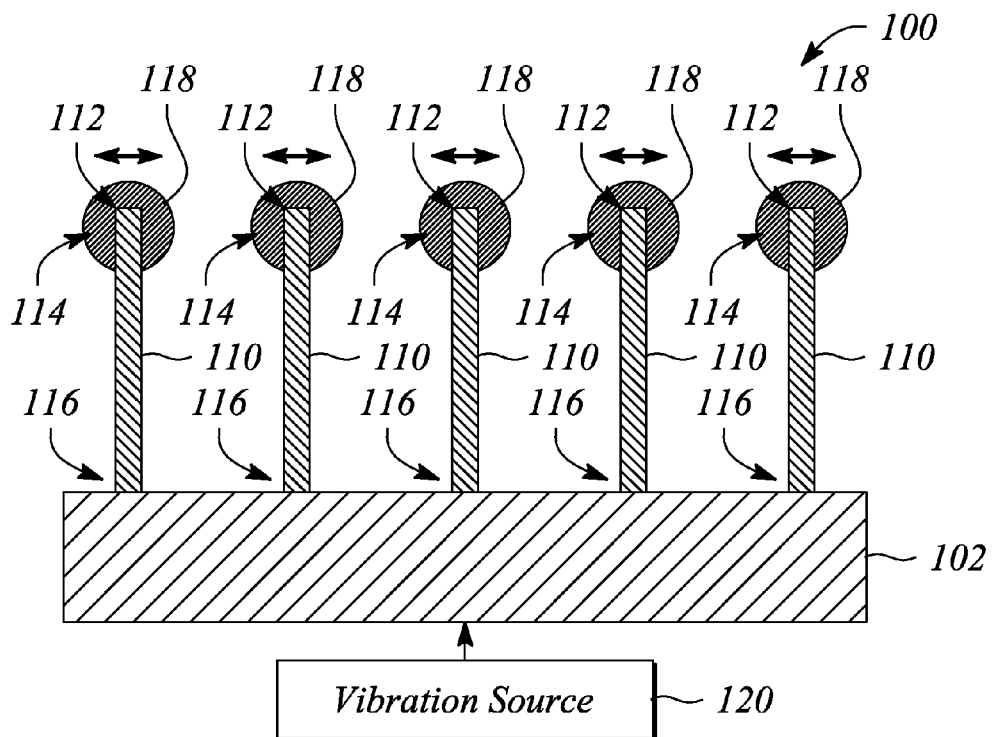
FIG. 1A illustrates a cross sectional view of a vibrating nanorod surface enhanced Raman spectroscopy (SERS) apparatus, according to an embodiment of the present invention.

Certain embodiments of the present invention have other features that are one of in addition to and in lieu of the features illustrated in the above-referenced figures. These and other features of the invention are detailed below with reference to the preceding drawings.

DETAILED DESCRIPTION

Embodiments of the present invention facilitate surface enhanced Raman spectroscopy (SERS). In particular, SERS according to various embodiments of the present invention is performed on or in a vicinity of a plurality of nanorods. The nanorods may enhance a signal strength of a Raman signal produced by Raman scattering from an analyte. In some embodiments, the analyte is adsorbed on the tips of the nanorods and electromagnetic fields associated with the tips may enhance the Raman signal generated by Raman scattering from the adsorbed analyte. Further, embodiments of the present invention employ vibration of the nanorods in general and more specifically vibration in a vicinity of the tips of the nanorods. The vibration facilitates detection of the Raman signal by facilitating improvement of a signal-to-noise ratio (SNR) of the Raman signal received by a detector. Specifically, a synchronous detector may be employed to detect the Raman signal emitted by the analyte where the detector is synchronized to a vibration frequency of the vibrating tips. In addition, the nanorod vibration may facilitate adsorption of analytes by inducing fluidic turbulence in a vicinity of the nanorods. For example, the induced fluidic turbulence may mitigate or even substantially overcome diffusion-limited adsorption of analytes (e.g., analyte molecules) by the nanorods.

Embodiments of the present invention employ a plurality of nanorods to enhance production and detection of the Raman signal from an analyte. A 'nanorod' herein is defined as an elongated, nanoscale structure having a length (or height) that exceeds by more than several times a nanoscale cross sectional dimension (e.g., width) taken in a plane perpendicular to the length (e.g., length>10× width). In general, the length is much greater than the width or cross sectional dimension to facilitate inducing a vibration of the tip of the nanorod. In some embodiments, the length exceeds the cross sectional dimension (or width) by more than a factor of 5 or 10. For example, the width may be about 40 nanometers (nm) and the height may be about 400 nm. In another example, the width at a base of the nanorod may range between about 20 nm and about 100 nm and the length may be more than about a 1 micrometer (μm). In another example, the nanorod may be conical with a base having a width ranging from between about 100 nm and about 500 nm and a length or height that may range between about one and several micrometers.

In various embodiments, nanorods of the plurality may be grown (i.e., produced by an additive process) or produced by etching or a subtractive process. For example, the nanorods may be grown as nanowires using a vapor-liquid-solid (VLS) growth process. In another embodiment, the nanorods may be produced by using an etching process such as, but not limited to, reactive ion etching, to remove surrounding material leaving behind the nanorods. Various techniques used in the fabrication of micro-electromechanical systems (MEMS) and nano-electromechanical systems (NEMS) are applicable to the fabrication of the nanorods.

Further, as used herein, the article 'a' is intended to have its ordinary meaning in the patent arts, namely 'one or more'. For example, 'a nanorod' means one or more nanorods and as such, 'the nanorod' explicitly means 'the nanorod(s)' herein. Also, any reference herein to 'top', 'bottom', 'upper', 'lower', 'up', 'down', 'front', back', 'left' or 'right' is not intended to be a limitation herein. Herein, the term 'about' when applied to a value generally means plus or minus 10% unless otherwise expressly specified. Moreover, examples herein are intended to be illustrative only and are presented for discussion purposes and not by way of limitation. Co-pending U.S. patent application Ser. No. 12/697,156, of Kuo et al., entitled "Vibrating Tip Surface Enhanced Raman Spectroscopy," filed concurrently herewith, is incorporated by reference in its entirety herein.

Figure 1B:
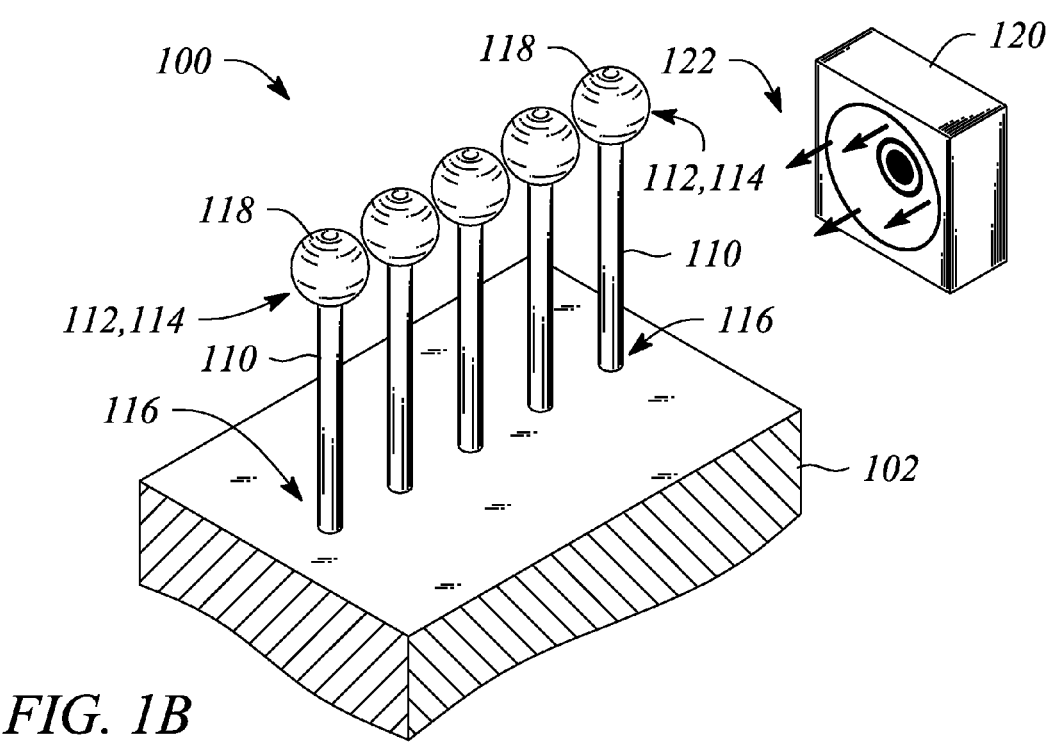
FIG. 1B illustrates a perspective view of the vibrating nanorod SERS apparatus illustrated in FIG. 1A, according to an embodiment of the present invention.

FIG. 1A illustrates a cross sectional view of a vibrating nanorod surface enhanced Raman spectroscopy (SERS) apparatus 100, according to an embodiment of the present invention. FIG. 1B illustrates a perspective view of the vibrating nanorod SERS apparatus 100 illustrated in FIG. 1A, according to an embodiment of the present invention. In particular, the SERS apparatus 100 is illustrated on a substrate 102. An analyte may be introduced to and analyzed by the SERS apparatus 100, according to some embodiments. For example, the analyte may be introduced by flowing a gas or a liquid containing the analyte along or above the substrate 102. In some embodiments, the analyte is adsorbed onto a surface of the vibrating nanorod SERS apparatus 100. A Raman signal produced by the adsorbed analyte is detected and analyzed to facilitate analysis (e.g., identification of) the analyte, according to some embodiments.

According to various embodiments, the vibrating nanorod SERS apparatus 100 comprises a plurality of nanorods 110 arranged in an array. As illustrated, each nanorod 110 is attached to the substrate 102 at one end (i.e., fixed end 116). In some embodiments, the nanorod 110 is rigidly attached to the substrate 102. Further, each nanorod 110 has a tip 112 at a free end 114 that is opposite the fixed end 116 of the nanorod 110 that is attached to the substrate 102. The tip 112 is configured to adsorb the analyte, according to some embodiments. The free end 114 is configured to vibrate back-and-forth (i.e., side-to-side) at a vibration frequency. The nanorod vibration may exhibit a resonance.

According to some embodiments, the tip 112 may either be substantially flattened or have rounded (i.e., domed) shape. For example, the nanorod 110 may have a tip 112 that results naturally from a process (e.g., V-L-S growth) used to realize the nanorod 110. In other example, the tip 112 may be further processed to impart a particular shape to the free end 114 of the nanorod 110. The tips 112 of the nanorods 110 may be flattened using chemical-mechanical polishing, for example.

In other embodiments, the tip 112 is substantially sharp (not illustrated). By 'sharp' it is meant that the tip 112 tapers from a cross sectional size of the nanorod 110 to an edge or a point at an end of the tip 112. The edge or the point generally has a relatively acute angle of inflection between surfaces of the tip 112 leading up to the edge or the point. In other words, a cross sectional size of the tip 112 in a vicinity of the end of the tip 112 (i.e., the edge or the point) is much smaller than an overall cross sectional size of the nanorod 110 away from the tip end. As such, the nanorod 110 having a tip 112 that is substantially sharp distinguishes it from other nanorods 110 having rounded or flat tips.

In some embodiments, the tip 112 may comprise a nanoparticle 118 attached to the free end 114 of the nanorod 110 (e.g., as illustrated in FIGS. 1A-1B). In some embodiments, a material of the nanoparticle 118 may differ from a material of the nanorod 110. In some of these embodiments, the nanoparticle 118 may be configured to one or both of enhance Raman scattering and facilitate analyte adsorption. In particular, in some embodiments, the nanoparticle 118 comprises a Raman-active material. For example, the nanoparticle 118 may comprise a Raman-active material such as, but not limited to, gold (Au), silver (Ag), and copper (Cu) having nanoscale surface roughness.

Figure 2A:
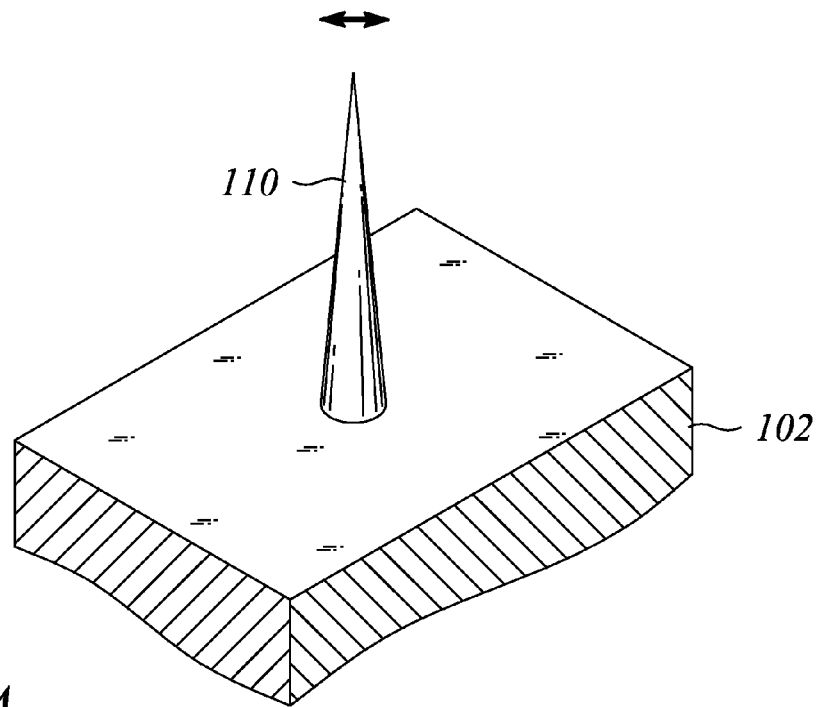
FIG. 2A illustrates a perspective view of a nanorod having a generally tapered shape, according to an embodiment of the present invention.

In some embodiments of the present invention, the nanorods 110 have a generally tapered shape compared to that illustrated in FIGS. 1A and 1B. FIG. 2A illustrates a perspective view of a nanorod 110 having a generally tapered shape, according to an embodiment of the present invention. In particular, as illustrated in FIG. 2A, the tapered shape of the nanorod 110 is conical. In other embodiments (not illustrated), the tapered shape may be generally faceted or pyramidal, for example having three, four, or more facets or sides. In yet other embodiments, the tapered shape may have a curvilinear perimeter when considering a cross section perpendicular to a long axis of the nanorod 110.

In other embodiments such as that illustrated in FIGS. 1A and 1B, the nanorod 110 has a columnar shape. The columnar portion may have either curvilinear or faceted perimeter in cross section. In particular, with respect to a cross section taken in a plane perpendicular to the long axis of the nanorod 110 and within the columnar portion, the columnar-shaped nanorod 110 may have a cross section that is characterized by either a curvilinear perimeter or a polygonal perimeter. For example, the columnar-portion may have a triangular cross section, a rectangular cross section or a cross section with more than four sides. In another example, the columnar portion may have a perimeter that is circular, oval or similarly curvilinear (e.g., a square with rounded corners).

Figure 2B:
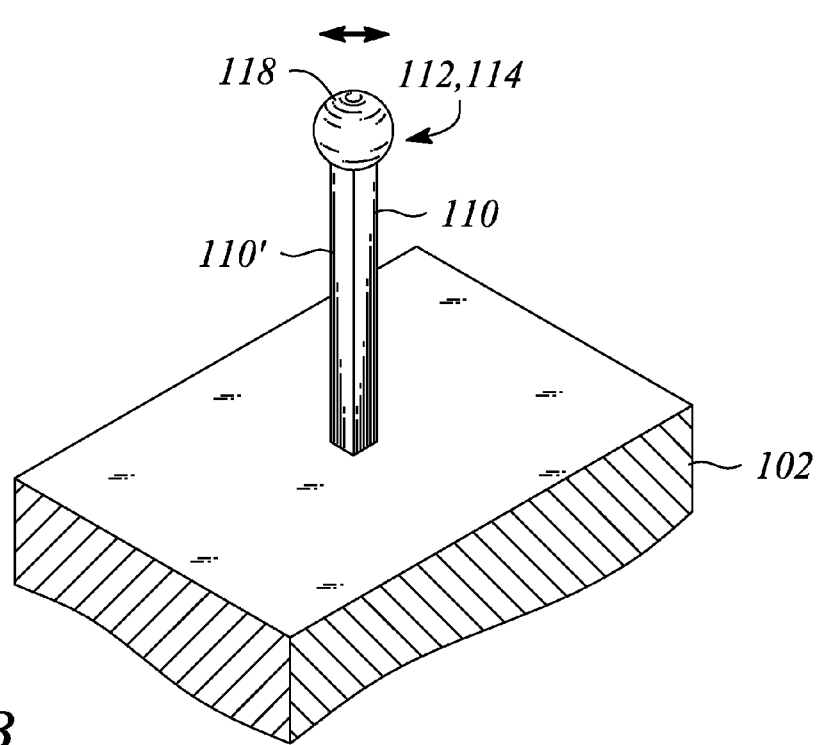
FIG. 2B illustrates a perspective view of a columnar-shaped nanorod, according to another embodiment of the present invention.

FIG. 2B illustrates a perspective view of a columnar-shaped nanorod 110, according to another embodiment of the present invention. A columnar portion 110' of the columnar-shaped nanorod 110 extends from the substrate to near the tip 112. In the vicinity of the tip 112, the columnar portion 110' is replaced by or gives way to the nanoparticle 118, as illustrated in FIG. 2B. As illustrated, the columnar-shaped nanorod 110 has a rectangular cross section within the columnar portion 110' while the nanoparticle 118 has a generally rounded shape (e.g., spherical).

The nanorod 110, whether tapered or columnar, generally has a long narrow profile that extends up from the attachment point to the substrate 102. The long narrow shape facilitates inducing vibration of the tip 112 which is described below. In particular, the nanorod 110 may be greater than about 5 times as long as it is wide (or thick), according to some embodiments. In some embodiments, the nanorod 110 may be greater than five to ten times as long as it is wide. For example, the nanorod 110 may have a width between several nanometers (nm) and about 100 nm and a length that is between about 500 nm and about 1 micron (μm).

In some embodiments, the nanorod 110 comprises a Raman-active material. By definition herein, a Raman-active material is a material that facilitates Raman scattering and the production or emission of the Raman signal from an analyte adsorbed on or in a surface layer or the material during Raman spectroscopy. Examples of Raman-active materials include, but are not limited to, gold (Au), silver (Ag), and copper (Cu). In some embodiments, the Raman-active materials comprise a layer or layers having nanoscale surface roughness. Nanoscale surface roughness is generally characterized by nanoscale surface features on the surface of the layer(s). Nanoscale surface roughness may be produced spontaneously during deposition of the Raman-active material layer(s) (e.g., gold deposition), for example.

In some embodiments, the nanorod 110 may comprise a semiconductor. For example, the semiconductor may comprise silicon (Si) or germanium (Ge) or an alloy of Si and Ge. In other examples, the semiconductor may comprise gallium arsenide (GaAs), indium gallium arsenide (InGaAs), and gallium nitride (GaN), as well as various other III-V, II-VI, and IV-VI compound semiconductors. In some of these embodiments, the semiconductor may be doped to render the semiconductor more conductive than an intrinsic or undoped (e.g., unintentionally doped) form of the semiconductor. For example, the Si may be doped with phosphorus (P), an n-type dopant, or boron (B), a p-type dopant, to increase the conductivity. Increasing the conductivity of the semiconductor within the nanorod 110 may facilitate inducing vibration using an electric field, which is described below, for example.

In some embodiments, the nanorods 110, or at least a portion thereof, are coated with a layer of Raman-active material (not illustrated). For example, the nanorods 110 may be coated with a layer of metal such as, but not limited to, gold (Au), silver (Ag) or copper (Cu) since these metals are know as Raman-active materials in conventional SERS. In some embodiments, the layer of Raman-active material is relatively thin compared to a width or thickness of the nanorod(s) 110. For example, the Raman-active material layer may have a width that is less than about 1/10 of the width of the nanorod 110. The Raman-active material layer 118 may be approximately 5-10 nm wide, for example.

In some embodiments, the Raman-active material layer may be confined to or localized in a vicinity of the tips 112 of the nanorods 110. In other embodiments, the Raman-active material layer may extend along more of a length of the nanorods 110 than just a vicinity of the tip 112. For example, an entire length of the nanorods 110 may be coated with the Raman-active material layer, according to some embodiments. In some embodiments, the Raman-active material layer (e.g., metal) may be annealed or otherwise treated to increase nanoscale surface roughness of the Raman-active material layer after deposition. Increasing the surface roughness may enhance Raman scattering from an adsorbed analyte, for example. In some embodiments, the Raman-active material layer comprises a layer or layers of nanoparticles. For example, a monolayer of gold (Au) nanoparticles may be used to coat the nanorods 110 and produce the Raman-active material layer. The layer(s) of nanoparticles may provide a nanoscale roughness that enhances Raman scattering, for example. In some embodiments, the Raman-active layer may additionally coat the nanoparticle 118 attached to the tip 112 of the nanorods 110.

In some embodiments, a surface of the nanorod 110 may be functionalized to facilitate adsorption of the analyte. For example, the tip 112 or portion of the nanorod 110 in a vicinity thereof (not illustrated) may be functionalized with a binding group to facilitate binding with a specific target analyte species. A surface of the Raman-active material layer on the nanorod 110 at the tip may be functionalized, for example. In another example, a surface of the nanoparticle 118 attached to the nanorod 110 may be functionalized. The functionalized surface (i.e., either a surface of the nanorod 110 itself, a Raman-active material layer coating on one or both of the nanorod 110 and the nanoparticle 118 attached to the tip 112) may provide a surface to which a particular class of analytes is attracted and may bond or be preferentially adsorbed. The functionalized surface may selectively bond with protein, DNA or RNA, for example.

In some embodiments, the nanorods 110 of the plurality are arranged in a linear array. For example, FIG. 1B illustrates a linear array of nanorods 110. In other embodiments, the array may be a two dimensional (2D) array. Exemplary 2D arrays may exhibit three-fold, four-fold, and even higher levels of symmetry, for example. An exemplary 2D array may have nanorods 110 arranged in equally spaced, linear rows and columns, for example. Another exemplary 2D array may be characterized by a triangular arrangement of the nanorods 110. In yet another exemplary 2D array may have nanorods 110 arranged in a substantially random or disordered array.

Referring again to FIGS. 1A and 1B, the vibrating nanorod SERS apparatus 100 further comprises a vibration source or a means for vibrating 120 the free end 114 of the nanorods 110. The means for vibrating 120 is configured to induce a vibration of the free end 114 of the nanorods 110 at the vibration frequency. In particular, the means for vibrating 120 is configured to produce a back-and-forth motion of the free end 114 (e.g., a side-to-side motion) as illustrated by a double-headed arrows in FIG. 1A. Vibration of the nanorods 110 at the vibration frequency may facilitate detection of a Raman scattering signal from the analyte adsorbed on the tips 112 of the nanorods 110, in some embodiments. Further in configuring the means for vibrating 120, consideration of a resonant frequency of vibration of the nanorods 110 may be advantageously employed. In particular, selecting a vibration frequency of the means for vibrating 120 to correspond to a resonant vibration frequency of the nanorods 110 may facilitate inducing vibration.

In some embodiments, the means for vibrating 120 may be configured to provide an acoustic vibration of the nanorods at the vibration frequency. In particular, the means for vibrating 120 may comprise an acoustic transducer. The acoustic transducer may be coupled to the nanorods 110 by air or another fluid surrounding the nanorods 110, for example. FIG. 1B illustrates coupling between the means for vibrating 120 (illustrated as an acoustic transducer 120) and the nanorods 110 through an exemplary acoustic wave 122 (illustrated by heavy arrows) in air or another fluid. In another example, the acoustic transducer may be mechanically coupled to (e.g., in direct contact with) the substrate 102 such that the acoustic vibration is communicated to the nanorods 110 through the substrate 102. FIG. 1A illustrates such an exemplary mechanical coupling between the means for vibrating 120 and the substrate 102. In some embodiments, the means for vibrating 120 (or acoustic transducer) may comprise a piezoelectric transducer 120 attached to the substrate 102. In other embodiments, the substrate 102 itself may comprise a piezoelectric material and serve as the piezoelectric transducer 120.

In some embodiments, the means for vibrating 120 comprises an alternating current (AC) electric field that couples electromagnetically to the nanorods 110 (not illustrated). Specifically, the AC electric field comprises an alternating or varying electric field value. The AC electric field is characterized by a frequency and a magnitude where the frequency represents or establishes a rate at which the electric field is varying. The AC electric field is configured to induce a vibration of the nanorods 110 and more particularly is configured to induce a vibration of the free end 114 and the tip 112 of the nanorod 110 and thus, is another embodiment of the means for vibrating 120.

For example, the AC electric field may comprise a pair of electric field values. A first value of the exemplary electric field may exert a force on the free ends 114 of the nanorods 110 in a first direction (e.g., to the left). Similarly, a second value of the exemplary electric field may exert a force on the free ends 114 of the nanorods 110 in a second direction (e.g., to the right). For example, the first value of the exemplary AC electric field may attract charges bound within a structure of the nanorods 110 while the second value may repel those same charges. Alternating between the first and second exemplary values in a periodic manner induces a back-and-forth motion of the free end 114 of the nanorods 110 as indicated by the double-headed arrow illustrated above the nanorods 110 in FIG. 1A. The back-and forth-motion constitutes the induced vibration of the free end 114 and the tip 112 of the nanorods 110.

In configuring the AC electric field to act as the means 120 for vibrating that induces vibration of the nanorods 110, the AC electric field may be switched abruptly between the pair of values (e.g., using a binary switching profile), according to some embodiments. In other embodiments, another switching profile that varies across a range of electric field values may be employed such as, but not limited to, a sinusoidal profile, triangular profile or sawtooth profile.

In some embodiments, the AC electric field may be provided by a pair of electrodes. The nanorods 110 (e.g., as a linear array) may be disposed between the pair of electrodes, according to some embodiments. In some embodiments, the AC electric field is provided by a charge difference or an electric potential difference (e.g., a voltage difference) between the electrodes. In other embodiments, a potential difference that provides the AC electric field is between the nanorods 110 and one or both of the electrodes of the pair.

Figure 3:
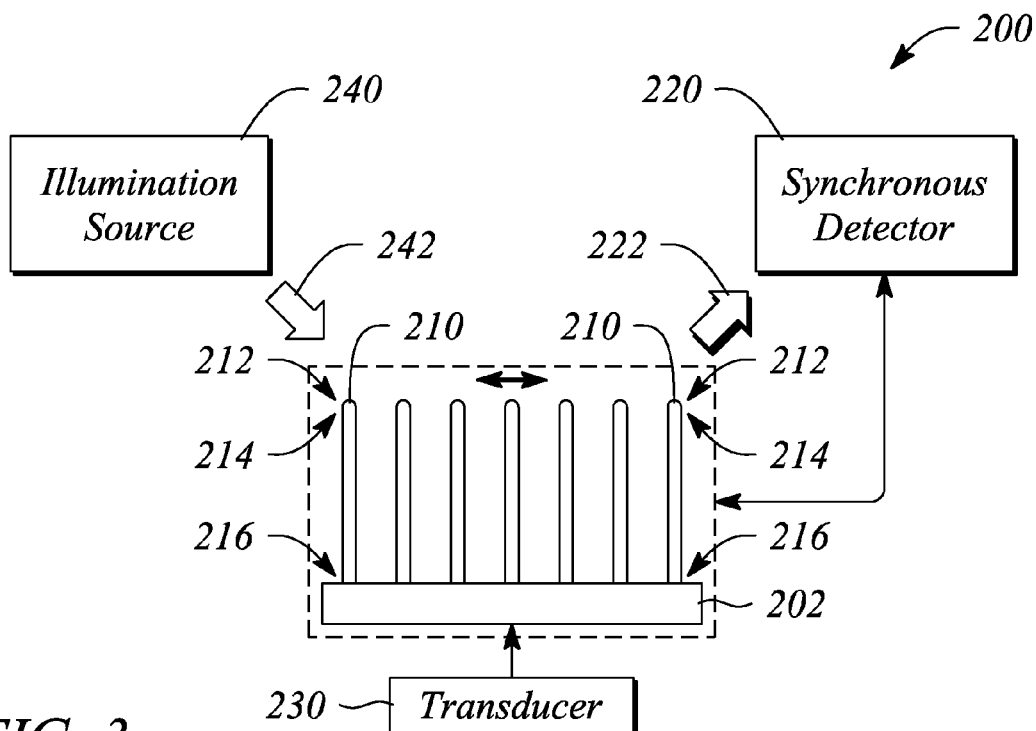
FIG. 3 illustrates a block diagram of a vibrating nanorod surface enhanced Raman spectroscopy (SERS) system, according to an embodiment of the present invention.

FIG. 3 illustrates a block diagram of a vibrating nanorod surface enhanced Raman spectroscopy (SERS) system 200, according to an embodiment of the present invention. The vibrating nanorod SERS system 200 comprises a plurality of nanorods 210. Each of the nanorods 210 has a tip 212 at a free end 214 of the nanorod 210. The tips 212 are configured to adsorb an analyte. Additionally, the tips 212 may facilitate production of a Raman signal emitted by the analyte. In particular, the tips 212 may concentrate or otherwise enhance an electromagnetic field in a vicinity of the tips 212 that enhances a magnitude of the emitted Raman signal. At fixed ends 216 opposite the free ends 214, the nanorods 210 are rigidly attached to a substrate 202. The rigid attachment of the nanorods 210 to the substrate 202 enables the free ends 214 and the tips 212 of the nanorods 210 to vibrate. The vibration has a vibration frequency determined by characteristics (length, mass, stiffness, etc.) of the nanorods 210. The vibration frequency of the nanorods 210 may have or exhibit a resonance frequency. In some embodiments, different ones of the nanorods 210 have one or both of different vibration frequencies and different resonant frequencies than other nanorods 210 of the plurality.

In some embodiments, the nanorods 210 of the plurality are arranged in a linear array. In other embodiments, the nanorods 210 are arranged in a two dimensional (2D) array. In some embodiments, a nanorod 210 of the plurality further comprises a nanoparticle (not illustrated) attached to the tip 212 of the nanorod 210. The nanoparticle, when present, is configured to facilitate analyte adsorption, in some embodiments. In some embodiments, the nanoparticle may one or both of facilitate production of the Raman signal and enhance production of the Raman signal. In some embodiments, the tips 212 of the nanorods 210 comprise a Raman-active material layer coating. The Raman-active material layer coating (e.g., a metal such as, but not limited to, gold, silver, copper, etc.) is configured to further enhance production of the Raman signal by the analyte adsorbed on or in a vicinity of the tips 212. In some embodiments, one or both of the Raman-active material layer coating and the nanoparticle attached to the tip 212 of the nanorods 210 are functionalized to further facilitate analyte adsorption.

As illustrated in FIG. 3, the vibrating nanorod SERS system 200 further comprises a synchronous detector 220. The synchronous detector 220 is configured to receive the Raman signal 222 from the analyte adsorbed on the tips 212 of the nanorods 210. In particular, the synchronous detector 220 is gated cooperatively with the vibration of the nanorod tips 212, in some embodiments. Cooperatively gating the synchronous detector 220 with the vibration may improve a signal-to-noise ratio (SNR) of the received Raman signal, according to some embodiments.

In particular, as the tips 212 of the nanorods 210 vibrate, an angle of Raman scattering from the analyte will vary. As a result, an intensity or magnitude of the Raman signal received by the synchronous detector 220 will vary as a function of the vibration. Cooperatively gating the synchronous detector 220 to coincide with a maximum received magnitude of the Raman signal 222 may maximize the SNR relative to a background signal, for example. FIG. 3 illustrates a connection (i.e., a lead line with double headed arrow) between the synchronous detector 220 and the plurality of nanorods 210 to emphasize the cooperative nature of the gating of the synchronous detector 220.

In some embodiments, the vibrating nanorod SERS system 200 further comprises a transducer 230. In some of these embodiments, the transducer 230 is attached to the substrate 202. The transducer 230 is configured to produce an acoustic vibration of the nanorods 210, in some embodiments. In other embodiments, the transducer 230 is not attached to the substrate 202 but is instead coupled or otherwise communicated to the nanorods 210 (e.g., through a connecting fluid). In yet other embodiments, the vibrating nanorod SERS system further comprises electrodes (not illustrated) that are configured to cooperatively provide an alternating current (AC) electric field. The provided AC electric field is configured to induce a vibration of the nanorod tips 212. In some embodiments, the nanorods 210 and either the transducer 230 or the electrodes are substantially similar to the nanorods 110 and the means for vibrating 120, respectively, described above with respect to the vibrating nanorod SERS apparatus 100.

In some embodiments, the vibrating nanorod SERS system 200 further comprises a voltage source (not illustrated). For example, the voltage source may be connected to the transducer 230. In another example, the voltage source may be connected to the electrodes (not illustrated) to provide the AC electric field. The voltage source may provide an alternating current (AC) voltage to either the transducer 230 or the electrodes, for example. In embodiments that employ a voltage source, the synchronous detector 230 may be synchronized to the voltage source. In some embodiments, the AC voltage may be directly communicated to the synchronous detector 230 (e.g., via a connection such as the double headed arrow illustrated in FIG. 3) to facilitate the cooperative gating.

According to some embodiments, the vibrating nanorod SERS system 200 further comprises an illumination source 240. The illumination source 240 provides an electromagnetic signal 242 that illuminates the analyte adsorbed on the tips 212 of the nanorods 210. The illumination causes Raman scattering and stimulates emission of the Raman signal 222 by the analyte. The illumination source 240 may be a laser 240 that illuminates the tips 212 with an optical signal 242, for example. In some embodiments, a frequency of the electromagnetic signal 242 is varied during illumination of the analyte. For example, an optical frequency of the laser 240 may be scanned or chirped across a band of frequencies. In another example, the electromagnetic signal 242 may be pulsed to produce a broadband electromagnetic signal.

Figure 4:
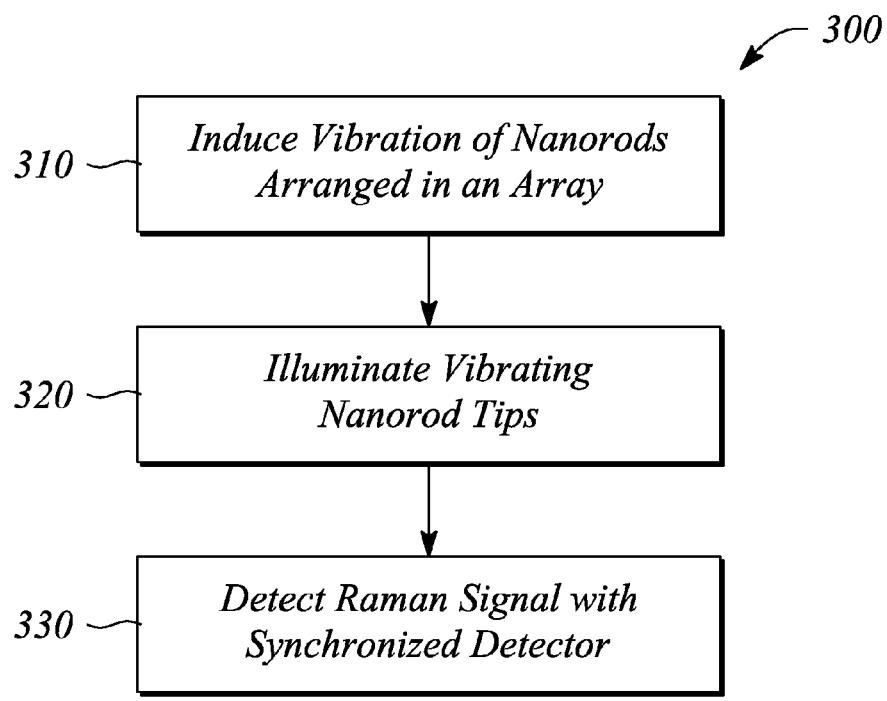
FIG. 4 illustrates a flow chart of a method of surface enhanced Raman spectroscopy (SERS) employing vibrating nanorods, according to an embodiment of the invention.

FIG. 4 illustrates a flow chart of a method 300 of surface enhanced Raman spectroscopy (SERS) employing vibrating nanorods, according to an embodiment of the invention. The method 300 of SERS employing vibrating nanorods comprises inducing 310 a vibration of a plurality of nanorods arranged in an array. According to various embodiments, each nanorod has a tip at a free end opposite an end of the nanorod that is attached to a substrate. The induced vibration produces a back-and-forth motion of the tips of the nanorods. For example, inducing 310 may comprise applying an acoustic sign to the nanorods of the plurality. Applying may be accomplished by a piezoelectric transducer connected to the substrate, for example. In another example, an acoustic transducer is coupled to and used to induce 310 vibration in the plurality of nanorods through air or a fluid that surrounds the nanorods.

In some embodiments, the nanorods are substantially similar to the nanorods described above with respect to the vibrating nanorod SERS apparatus 100. In particular, in some embodiments, the nanorods comprise a tapered shape, the nanorod being widest at the end of the nanorod adjacent to the substrate and tapering to the tip. In other embodiments, the nanorods have a columnar shape.

In some embodiments, tips of the nanorods comprise one or more nanoparticles. The nanoparticle(s) may facilitate adsorption of the analyte and may further facilitate production of a Raman signal from the analyte. Further, in some embodiments, the tip of the nanorod has a Raman-active material layer coating. In some of these embodiments, the Raman-active material layer coating comprises a conductive metal. For example, the conductive metal may comprise, but is not limited to, one or more of gold (Au), silver (Ag) and copper (Cu). In some embodiments, the Raman-active material layer coating may comprise one or more nanoparticles of the Raman-active material layer. In some embodiments, the nanorods comprise a semiconductor. For example, the nanorod may comprise one or more of silicon (Si), germanium (Ge), an alloy of Si and Ge, gallium arsenide (GaAs), titanium oxide (TiO), tin oxide (SnO), indium gallium arsenide (In-GaAs), and gallium nitride (GaN), as well as various other III-V, II-VI, and IV-VI compound semiconductors.

The method 300 of SERS employing vibrating nanorods further comprises illuminating 320 the vibrating tips of the nanorods. In some embodiments, the illumination 320 produces a Raman signal from an analyte adsorbed on the vibrating tip. The illumination 320 may be provided by an electromagnetic signal source (e.g., a laser), for example. The Raman signal is produced by Raman scattering by the analyte. In some embodiments, the tip enhances an electromagnetic field strength to increase a strength of the Raman signal produced by the illuminated analyte.

The method 300 of SERS employing vibrating nanorods further comprises detecting 330 the Raman signal. In some embodiments, detecting 330 the Raman signal comprises using a detector that is synchronized to the induced 310 vibration of the nanorods. In particular, characteristics of the detector may be synchronized to a frequency of the induced 310 vibration. For example, the detector may be gated in a manner that corresponds to a maximum or near maximum in a received Raman signal associated with an angular variation between the detector and the vibrating tip caused by the induced 310 vibration.

Thus, there have been described embodiments of a surface enhanced Raman spectroscopy (SERS) apparatus, a SERS system and a method of SERS that employ a plurality of nanorods arranged in an array, the nanorods having vibrating tips. It should be understood that the above-described embodiments are merely illustrative of some of the many specific embodiments that represent the principles of the present invention. Clearly, those skilled in the art can readily devise numerous other arrangements without departing from the scope of the present invention as defined by the following claims.

What is claimed is:

1. A vibrating nanorod surface enhanced Raman spectroscopy (SERS) system comprising:
   a plurality of nanorods arranged as an array on a substrate surface, each of the nanorods having a tip at a free end opposite to an end of the nanorods that is rigidly attached to a substrate, the tips of the nanorods being configured to adsorb an analyte and to facilitate production of a Raman signal emitted by the analyte; and
   a synchronous detector configured to receive the Raman signal from the analyte adsorbed on the tip of the nanorod,
   wherein the tips of the nanorods are configured to vibrate at a vibration frequency, and wherein the synchronous detector is configured to be gated cooperatively with the vibration of the nanorod tips.

2. The vibrating nanorod SERS system of claim 1, wherein the nanorods of the plurality are arranged in a linear array.

3. The vibrating nanorod SERS system of claim 1, further comprising a transducer attached to the substrate, the transducer being configured to produce an acoustic vibration of the nanorods.

4. The vibrating nanorod SERS system of claim 1, wherein the nanorods further comprise a nanoparticle attached to the tip, the nanoparticle being configured to adsorb the analyte.

5. The vibrating nanorod SERS system of claim 1, further comprising an illumination source configured to illuminate the tips of the nanorods.

6. The vibrating nanorod SERS system of claim 1, wherein the tips of the nanorods comprise a Raman-active material layer configured to further enhance the Raman signal emitted by the analyte.

7. A method of surface enhanced Raman spectroscopy (SERS) employing vibrating nanorods, the method comprising:
- inducing a vibration of a plurality of nanorods arranged in an array, each nanorod having a tip at a free end opposite to an end of the nanorod that is attached to a substrate, the vibration producing a back-and-forth motion of the tips of the nanorods;
- illuminating the vibrating tips of the nanorods, the illumination producing a Raman signal from an analyte adsorbed on the vibrating tips; and
- detecting the Raman signal using a detector that is synchronized to the induced vibration of the nanorods.

8. The method of SERS employing vibrating nanorods of claim 7, wherein inducing a vibration comprises applying an acoustic signal to the nanorods of the plurality.

9. The method of SERS employing vibrating nanorods of claim 7, wherein the nanorod tips have a Raman-active material layer coating, the Raman-active material layer coating comprising one or more of gold, silver and copper.

10. A vibrating nanorod SERS system, comprising:
- a plurality of nanorods arranged in an array, each nanorod having a tip at a free end opposite to an end of the nanorod that is attached to a substrate, the tip being configured to adsorb an analyte, the free end being configured to vibrate at a vibration frequency;
- a vibration source configured to induce a vibration of the free end of the nanorods at the vibration frequency, the vibration source producing a back-and-forth motion of the free end of the nanorods;
- an illumination source configured to illuminate the tips of the nanorods; and
- a synchronous detector configured to receive a signal scattered from the tips of the nanorods, the synchronous detector being further configured to be gated at the vibration frequency;
- wherein the vibration of the nanorods at the vibration frequency is configured to facilitate detection of a Raman scattering signal emitted by the analyte adsorbed on the tips of the nanorods, and the gating of the synchronous detector is configured to further facilitate detection of the Raman scattering signal produced by an illuminated analyte adsorbed on the tips.

11. The vibrating nanorod SERS system of claim 10, wherein the vibration of the tips moves analyte particles adsorbed on the tips in and out of an illumination beam of the illumination source.

* * * * *